United States Patent [19]
Nix, Jr.

[11] Patent Number: 4,884,296
[45] Date of Patent: Dec. 5, 1989

[54] PROTECTIVE FACE SHIELD

[75] Inventor: Frank H. Nix, Jr., Gainesville, Ga.

[73] Assignee: Delta Medical Systems, Inc., Alpharetta, Ga.

[21] Appl. No.: 275,717

[22] Filed: Nov. 23, 1988

[51] Int. Cl.4 .............................................. A61F 9/00
[52] U.S. Cl. ................................................ 2/011; 2/9
[58] Field of Search ..................... 2/9, 11, 12, 15, 452, 2/454, DIG. 11

[56] References Cited

U.S. PATENT DOCUMENTS

| | | | |
|---|---|---|---|
| D. 199,931 | 12/1964 | Kline | D57/1 |
| 1,911,817 | 5/1933 | DuBois | 2/9 |
| 2,330,442 | 9/1943 | Nero | 2/12 |
| 2,541,242 | 2/1951 | Grove | 2/13 |
| 2,614,255 | 10/1952 | Ellis | 2/454 X |
| 2,774,970 | 12/1956 | Dubois | 2/9 |
| 2,965,902 | 12/1960 | Louch | 2/9 |
| 3,015,105 | 1/1962 | Rogowski | 2/9 |
| 3,295,143 | 1/1967 | Hoffman | 2/9 X |
| 3,828,366 | 8/1974 | Conrad et al. | 2/174 |
| 4,084,585 | 4/1978 | Venaleck | 128/146 |
| 4,277,847 | 7/1981 | Florio | 2/DIG. 11 X |
| 4,621,378 | 11/1986 | Hatchman | 2/9 |
| 4,694,507 | 9/1987 | Owen | 2/9 X |
| 4,712,254 | 12/1987 | Daigle | 2/DIG. 11 X |

Primary Examiner—Werner H. Schroeder
Assistant Examiner—Jeanette E. Chapman
Attorney, Agent, or Firm—Thomas & Kennedy

[57] ABSTRACT

A protective face shield has a shield member of transparent flexible material in the upper corners of which pairs of slits are formed. A headband is threaded through the slits in a manner such that once the headband is donned the shield member may be pulled away from the wearer's face to provide good air circulation. A lower portion of the face shield is contoured inwardly to protect the throat.

2 Claims, 2 Drawing Sheets

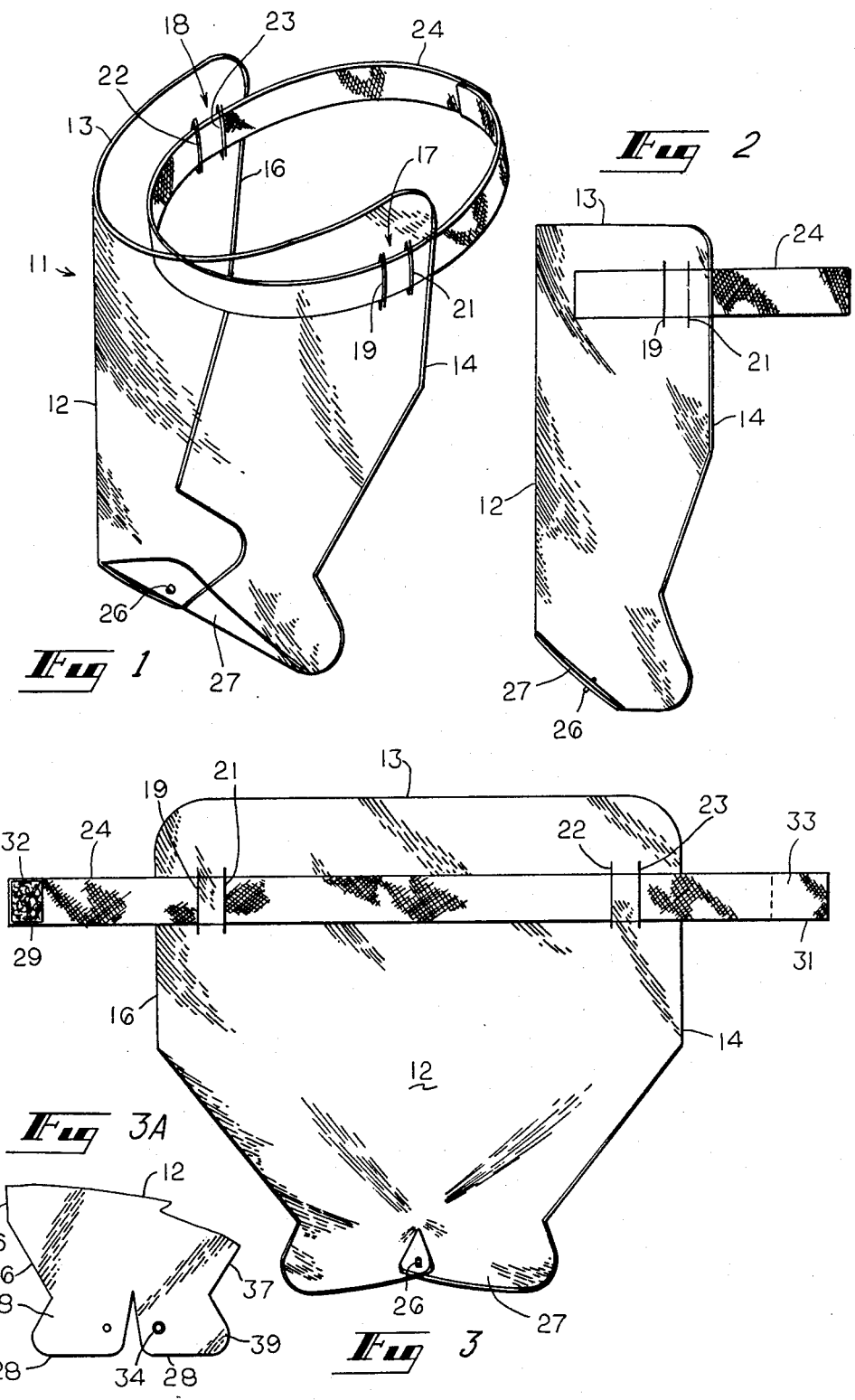

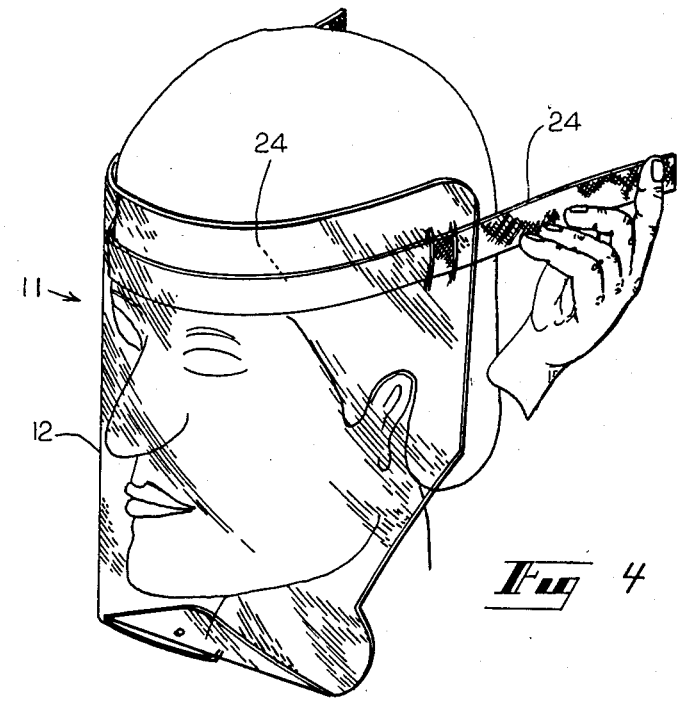
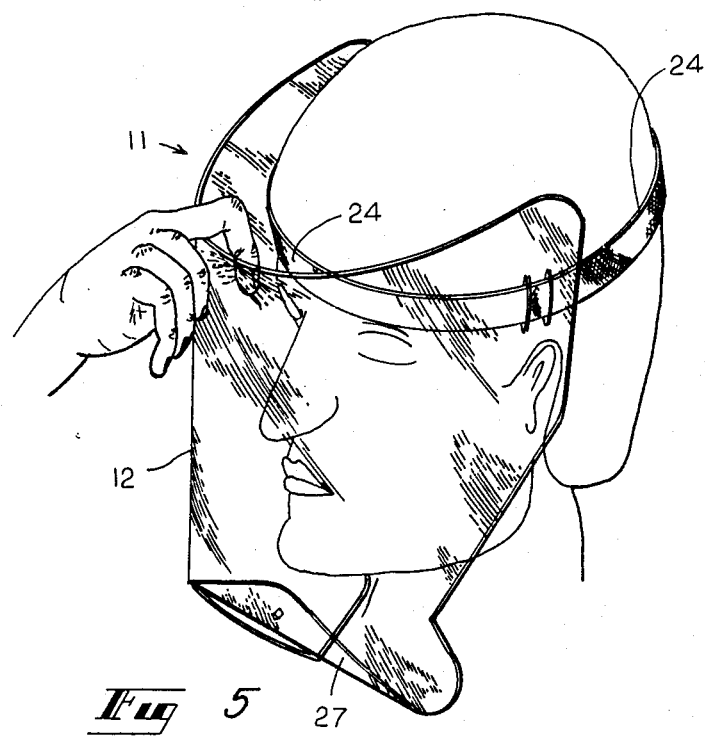

PROTECTIVE FACE SHIELD

TECHNICAL FIELD

This invention relates to face shields, and, more particularly, to a protective face shield for shielding the wearer's face from, for example, spray-laden atmosphere.

BACKGROUND OF THE INVENTION

Protective face masks are quite commonly used in surgical operating rooms, emergency treating rooms, chemical or other types of laboratories, and in dental treatment areas. These masks are intended primarily to protect the face of the wearer from spray of, for example, blood, saliva, or chemicals that are or can be harmful. The necessity of protecting the face has become even more acute with the outset of AIDS where the potential for transmission from one person to another is great. Furthermore, those called upon to treat AIDS patients need the reassurance that there is substantially total protection of the face from spray of even breath emanating from the patient.

Unfortunately, where total protection of the face is to be had, prior art masks or shields are, in general, made to fit tightly to the face of the wearer, thus causing heat and moisture build-up between the shield and the face. In addition to the discomfort engendered, the heat and moisture are especially bad where the wearer of the shield wears eye glasses, since the glasses tend to fog up, and, in order to eliminate such fogging, the shield must be removed from the wearer's face.

In U.S. Pat. No. 1,911,817 of DuBois, there is shown a face shield designed to protect the wearer from the sun's rays. The shield is attached to a headband, and projects outwardly therefrom so that a gap is formed between the wearer's face and the shield. Such an arrangement permits air circulation, lowering the heat build up. However, the face of the wearer, and more particularly, the lower portion and the underside of the lower jaw, are not protected from spray emanating from below the wearer's head.

A protective face mask is shown in U.S. Pat No. 3,828,366 of Conrad et al, which affords substantial protection to the face of the wearer, but which, in order to do so, overlies the face and conforms to the shape thereof. Inasmuch as the mask is made of impermeable plastic material, it can become quite uncomfortable, especially if worn for an extended period of time. In addition, eyeglass wearer's would have difficulty with such a mask since no provision is made for eyeglasses and the heat build up would soon, as pointed out heretofore, cause the glasses to fog up.

U.S. Pat. No. 2,774,970 of DuBois discloses a face shield which allows circulation of air, but which does not protect the entire face, nor does it accommodate eyeglass wearers.

In all of this prior art, a compromise has been made to insure protection of the entire face or provide for air circulation between the mask and the face. In all cases it is one or the other, but never both.

SUMMARY OF THE INVENTION

The present invention overcomes the shortcomings of the prior art by eliminating, through its unique structure, the necessity of compromise. Thus the present invention is a face shield which substantially completely protects the entire facial area, including the underside of the lower jaw, while at the same time allowing circulation of air between the wearer's face and the inside of the shield.

In a first preferred embodiment of the invention, a face shield is formed from a flat sheet of flexible plastic material and has an upper edge and first and second side edges. In each of the corner regions defined by the junction of the side edges and the upper edge are first and second slits in the plastic material which are substantially parallel to each other and to the side edges. A headband of suitable cloth or woven material, preferably elastic, is threaded through the slits in the face shield, and the ends of the headband have affixed thereto suitable fastening means, such as Velcro ®. The lower portion of the shield has a bottom edge having a V-shaped notch therein with mating fastening means on either side of the notch near the bottom edge.

In use, the fastening means adjacent the notch are fastened to each other, thereby pulling the sides of the notch together and causing that portion of the shield to slope down and away from the apex of the notch thereby displacing the bottom edge from the front of the shield forming a shield for the underside of the lower jaw of the wearer. Although it is not strictly necessary to shield the underside of the lower jaw, unless there are lesions thereon, such shielding prevents the intrusion of spray, for example, into the space between the shield and the face from below. The headband is fastened around the wearer's head, thereby causing the shield to curve around the face. The top edge of the shield is then pulled forward, away from the forehead, which is made possible by the slits in the shield. The elasticity of the headband and each portion of the shield between the two slits bearing against the wearer's temples serve to hold the shield in place during normal usage. Thus there is provided passage for air circulation between the wearer's face and the inside of the shield, which can be adjusted to suit the wearer. On the other hand, the shield protects the entire face, and by shielding the underside of the lower jaw, protects against spray directed toward the face from below. Thus there is provided substantially complete shielding of the face and air circulation for reducing heat and humidity between the shield and the face.

In another preferred embodiment of the invention, the face shield is molded from a piece of the plastic material so that that portion protecting the lower portions of the face is permanently shaped, and fastening means are not necessary.

These and other features and advantage of the present invention will be more readily apparent from the following detailed description, read in conjunction with the accompanying drawings.

DETAILED DESCRIPTION OF THE DRAWING

FIG. 1 is a perspective view of a preferred embodiment of the shield of the invention in its mounted configuration.

FIG. 2 is a side elevation view of the shield of FIG. 1.

FIG. 3 is a front elevation view of the shield of FIG. 1 with the ends of the head strap disconnected.

FIG. 3A is a plan view of a portion of the shield of FIG. 3 before the lower portion is fastened together.

FIG. 4 illustrates the first step in donning the shield.

FIG. 5 illustrates the second step in donning and adjusting the shield.

DETAILED DESCRIPTION

In FIGS. 1-5 there is shown a preferred embodiment of the invention comprising a face shield 11 having a shielding member 12 of a suitable, flexible, transparent plastic material. Although the material of shield member 12 is characterized as being flexible, it has sufficient stiffness to hold whatever shape it assumes by bending. Member 12 has a top edge 13 and first and second side edges 14, 16, forming first and second corner regions 17, 18 with top edge 13. In the corner regions 17 are first and second substantially parallel slits 19, 21 and in corner region 18 are first and second substantially parallel slits 22, 23. A headband 24 of suitable material, such as woven elastic material, which preferably is absorptive to water or sweat, is threaded through slits 19, 21 and 22, 23, as shown, and its ends, which will be discussed more fully in connection with FIG. 3, are joined together.

As can best be seen in FIG. 1 and 2, the lower portion of the shielding member 12 is divided into two portions which, when joined together by suitable fastening means 26, such as a rivet, pin, snap, or heat sealing, form a sloping, rearwardly extending portion 27. This portion 27 of the shielding member 12 actually extends under the lower jaw of the wearer, thereby protecting him from any spray or the like directed at him from below.

FIG. 3 depicts the headband 24 in greater detail while FIG. 3A shows in detail the configuration of bottom edge 28 of shielding member 12 prior to its being pinned or fastened to form sloping portion 27.

Headband 24 has mounted on its ends 29 and 31 suitable fastening means, such as, and preferable, first and second mating patches 32, 33 of Velcro ®. As shown in FIG. 3, patch 2 is mounted on the front of end 29 while patch 33, shown by dashed lines, is mounted on the rear so that patches 32 and 33 can mate. These Velcro ® patches, combined with the elasticity of band 24 give a wide range of adjustment to the headband size so that virtually any wearer can achieve a firm but comfortable fit.

As shown in FIG. 3A, edges 14 and 16 have angled portions 36 and 37, terminating in lobes 38 and 39. While this configuration is not essential, it makes the shield less cumbersome while insuring protection. Lower edge 28 has a large V-shaped notch 41 and fastening means 26 and 34 which may be pin or rivet and hole, or male and female snaps. As shown in FIG. 3A shield member 12 is essentially a flat member of flexible, transparent material, but when fastening members 26 and 34 are joined, assumes the configuration best seen is FIG. 2 results.

FIGS. 4 and 5 illustrate the basic steps for putting on the face shield. In FIG. 4 the headband is made to encircle the head and its ends are joined so that the headband fits comfortably. After the headband is fastened, the mask is pulled forward by simply hooking with a finger, as shown in FIG. 5, until the desired air circulation is achieved.

As was pointed out earlier, the shield member 12 may alternatively be molded to produce the sloping portion 27. Although a molded shield member 12 has not been shown, it is not believed to be necessary to do so, since the configuration would be the same as shown in FIGS. 1 through 3, without the pin or fasteners 26 and 34 and the small overlap. Other modifications, additions and deletions may be made without departure from the spirit and scope of the invention as set for in the following claims.

I claim:

1. A protective face shield comprising a shield member of transparent flexible material, said member having an upper edge and first and second side edges joining said upper edge to form two corner regions, said shield member further having a bottom edge displaced from the front of said shield member by a sloped portion of said shield member, said bottom edge being formed with a V-shaped notch therein, a pair of slits formed in each of said corner regions of said shield member, a headband slidably threaded through said pairs of slits and having first and second ends, fastening means on said headband at the ends thereof, and second fastening means on either side of said notch adjacent said bottom edge.

2. A protective face shield as claimed in claim 1 wherein said second fastening means comprises a pin mounted on one side of said notch and a matching mating hole on the other side of said notch.

* * * * *